United States Patent [19]

Müller et al.

[11] Patent Number: 5,167,451

[45] Date of Patent: Dec. 1, 1992

[54] METHOD AND DEVICE FOR THE THERMAL SHOCK TEST

[75] Inventors: Walter Müller; Joachim Naumann, both of Kelkheim; Ewald Preisegger, Nauheim; Martin Schnauber, Hofheim am Taunus, all of Fed. Rep. of Germany

[73] Assignee: Hoechst Aktiengesellschaft, Frankfurt am Main, Fed. Rep. of Germany

[21] Appl. No.: 742,632

[22] Filed: Aug. 8, 1991

[30] Foreign Application Priority Data

Aug. 10, 1990 [DE] Fed. Rep. of Germany ....... 4025348

[51] Int. Cl.⁵ ........................................... G01N 25/00
[52] U.S. Cl. ..................................... 374/45; 374/57
[58] Field of Search ..................................... 374/45, 57

[56] References Cited

U.S. PATENT DOCUMENTS 4,955,726 9/1990 Bargigia et al. .................... 374/57

FOREIGN PATENT DOCUMENTS

| 0147478 | 4/1981 | Fed. Rep. of Germany | 374/57 |
| 0144638 | 7/1985 | Japan | 374/57 |
| 0263836 | 12/1985 | Japan | 374/57 |
| 0272135 | 11/1987 | Japan | 374/57 |
| 0196535 | 8/1989 | Japan | 374/57 |
| 0010131 | 1/1990 | Japan | 374/57 |
| 0027234 | 1/1990 | Japan | 374/57 |
| 0877432 | 10/1981 | U.S.S.R. | 374/57 |
| 0894464 | 12/1981 | U.S.S.R. | 374/57 |

OTHER PUBLICATIONS

MIL-STD-883C, Notice 8, Method 1011.8, "Thermal Shock", (Feb. 12, 1989).

Primary Examiner—William A. Cuchlinski, Jr.
Assistant Examiner—W. Morris Worth

[57] ABSTRACT

The invention relates to a method for testing objects by thermal shock in a closed apparatus, comprising the following, preferably repeated steps:
 a) introducing the object to be tested into the apparatus,
 b) cooling the object by immersion in a liquid cold bath,
 c) drying the object above at least one cold trap or in at least one drying chamber,
 d) heating the object by immersion in a liquid hot bath and
 e) drying the object above at least one cold trap or in at least one drying chamber, the temperature difference between the hot bath and cold bath being 50 to 500 K., the temperature of the cold trap being 5–30 K. lower than the temperature of the cold bath and the temperature of the drying chamber being 10 to 50° C. higher than the temperature of the hot bath, and the steps b) to e) being carried out in mutually separated parts of the apparatus, which are connected to one another via closable openings. The invention also relates to a device for testing objects by thermal shock.

12 Claims, 4 Drawing Sheets

METHOD AND DEVICE FOR THE THERMAL SHOCK TEST

The present invention relates to a method and to a device for testing objects by thermal shock in a closed apparatus, wherein the object to be tested is immersed in a liquid cold bath for cooling, then passes through a cold trap or a drying chamber, is heated by immersion in a liquid hot bath and then passes through a drying chamber or a cold trap, and subsequently the thermal shock cycle is repeated.

In the thermal shock test, the resistance of objects, in particular of electronic components, to extreme temperature changes is determined, for example in order to detect mechanical weaknesses in the separation layers between materials in the case of chips and contact pins or to detect defects in housings of electronic articles. The test specimens are here alternately exposed to high and low temperatures. Thus, according to MIL-STD-883C, Notice 8, Method 1011.8 of Feb. 12, 1989 (U.S. Government), the test specimens are alternately immersed fifteen times, each time for at least five minutes, in a cold bath at 0° to −195° C. and then in a hot bath at +100° to +200° C., and the transport from the hot bath into the cold bath and vice versa should not take longer than ten seconds.

However, an important disadvantage is that, due to hot bath liquid or cold bath liquid adhering to the test specimen, the bath liquids are mixed during the frequent and rapid bath changes of the test specimens. If two different bath liquids are used for the hot bath and for the cold bath, precipitation of the hot bath liquid in the cold bath liquid can, for example, occur as a result of the mixing. Moreover, the generally low-boiling bath liquid, which is carried over from the cold bath with the test specimens and the basket into the hot bath, is inevitably heated and is thus partially lost due to vaporization. It is therefore in general advantageous to replace the two bath liquids by a single bath liquid having a wide liquid range. However, even the use of a single bath liquid in the cold bath and hot bath is not without problems, since the cold bath liquid can, because of its higher viscosity, be carried over into the hot bath during the transport of the test specimens in the basket, and this in turn can lead to a fall in the level in the cold bath and to overflowing of the hot bath. Moreover, the higher the viscosity of the cold bath liquid, the more the heat transfer in the cold bath is reduced, so that the required temperature in the cold bath cannot be maintained over a prolonged operating period.

It is now the object of the invention to provide a method and a device for thermal shock testing, in such a way that mixing of hot bath liquid and cold bath liquid is substantially avoided.

It has now been found that this mixing is substantially prevented by the installation of heat exchangers between the cold bath and hot bath.

It has also been found that the flow velocity and hence the heat transfer in the cold bath, especially in the case of highly viscous cold bath liquids having a kinematic viscosity in general greater than 150 mm$^2$/s, can be increased by the introduction of gaseous nitrogen into the bath liquid. In addition, the gaseous nitrogen forms an inert gas barrier for the vapors from the hot bath and, moreover, displaces water vapor from the system. This prevents the condensation of water vapor on the test specimens and in the cold bath.

It has also been found that the nitrogen gas, in general enriched thereby with cold bath vapors, can be largely purified by removal of the cold bath vapors by scrubbing with liquid nitrogen in counter-current in a downward-flow column, and that the temperature of the cold bath can be controlled via the feed rate of the liquid nitrogen which is introduced via the downward-flow column into the cold bath liquid.

It has also been found that the local circulation rate of the bath liquid can be increased by introducing the object to be tested into a pipe loop as the bath vessel, in which the bath liquid circulates.

One subject of the invention is a method for testing objects by thermal shock in a closed apparatus, comprising the following steps:

a) introducing the object to be tested into the apparatus through a closable opening, b) cooling the object by immersion in a liquid cold bath, c) drying the object above at least one cold trap or in at least one drying chamber, d) heating the object by immersion in a liquid hot bath and e) drying the object above at least one cold trap or in at least one drying chamber, the temperature difference between the hot and cold bath being 50 to 500 K (50° to 500° C.), the temperature of the cold trap being 5–30 K (5°–30° C.) lower than the temperature of the cold bath and the temperature of the drying chamber being 10 to 50 K (10° to 50° C.) higher than the temperature of the hot bath, and the steps b) to e) being carried out in mutually separated parts of the apparatus, which are connected to one another via closable openings.

The cold trap or the drying chamber used in step e) can be the same as in step c) or different ones. The steps b) to e) are repeated several times. It is therefore equally possible to start the cycle with step d) instead of with step b).

Preferably, the object to be tested is cooled by immersion in a liquid cold bath, dried above a cold trap, heated by imersion in a liquid hot bath and from there transported again via a drying chamber to the cold bath for further thermal shock cycles. In other words, it is preferable to use a cold trap in step c) and a drying chamber in step e).

The temperature difference between the hot and cold bath is preferably 100 to 350 K (100° to 350° C.), especially 150 to 250 K. If one or two cold traps are used, their temperature is in general 5 to 30 K (5° to 30° C.) lower than the temperature of the preceding bath. If one or two drying chambers are used, their temperature is preferably 10 to 20 K (10° to 20° C.) higher than the boiling point of the preceding bath. The liquids of the hot bath and of the cold bath can here be the same or different.

In a special embodiment which is particularly suitable for the use of one liquid for both baths, gaseous and/or liquid nitrogen is introduced into the cold bath liquid. Preferably, both are used and the gaseous nitrogen is introduced directly into the cold bath liquid, while the liquid nitrogen is introduced into the cold bath liquid via a downward-flow columns in counter-current to the gaseous nitrogen, the temperature of the cold bath in general being controlled via the feed rate of the liquid nitrogen.

In a further embodiment which is likewise suitable for the use of one liquid in both baths, at least one of the two bath vessels is formed as a pipe loop, in which the bath liquid circulates.

A further subject of the invention is a device for testing objects by thermal shock in a closed apparatus, comprising a 1st chamber with a cold bath and a device for cooling the latter, a 2nd chamber with a hot bath and a device for heating the latter, a heat exchanger zone, containing at least one drying chamber provided with a heating device and/or at leas tone chamber provided with a cold trap and a cooling device for the latter, the 1st chamber and the 2nd chamber being connected via the heat exchanger zone by means of closable openings, and a device for transporting the objects to be tested from the 1st chamber via the heat exchanger zone to the 2nd chamber or in the converse direction, including one or more closable openings on the outer wall of the apparatus for loading the transport device with the objects to be tested and for unloading the latter from the transport device.

The device according to the invention is also designated device 1 below.

The heat exchanger zone can be (FIG. 4), but does not have to be, a single coherent chamber area. If is contains only a drying chamber but no chamber with a cold trap, or only a chamber with a cold trap but no drying chamber, it naturally represents a single chamber area. If, however, the heat exchanger zone contains both types of chamber, these can be located directly side by side and be separated merely by a wall, or they can be further away from one another, i.e. occupy two separate chamber areas.

Preferably, if a cold trap is used, a two-stage compression refrigeration unit is used for cooling the cold bath and the cold trap, the cold bath being cooled by the first vaporizer stage at a higher temperature level and the cold trap being cooled by the second vaporizer stage at a lower temperature level.

A further special embodiment of the device 1 uses, for the cold bath, a vessel with a double bottom, the upper bottom thereof being preferably constructed as a perforated plate. The nitrogen gas introduced between the two bottoms flows through this perforated plate in a finely disperse form into the cold bath liquid. The installation of an additional agitator can in general be omitted in this embodiment.

A further special embodiment of the device 1 has, as the cold bath and/or as the hot bath, a pipe loop with a circulating bath liquid.

The advantages achieved by the invention are especially that the hot bath liquid and cold bath liquid are largely not mixed with one another. Particularly good heat transfer is achieved in the cold bath by the two latter special embodiments. They should therefore preferably be applied when on liquid is used for both baths.

Figure 1:
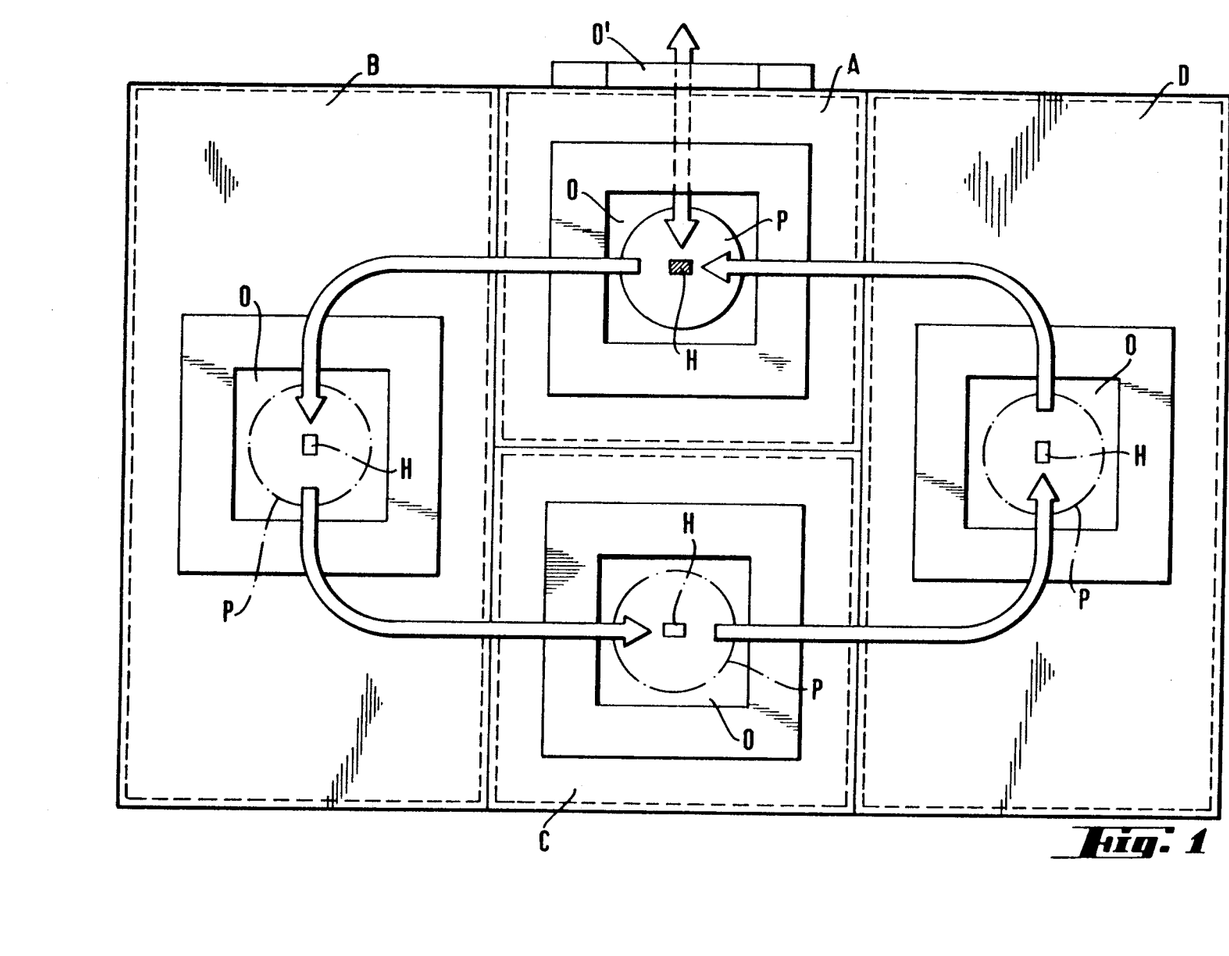
FIG. 1 is a diagrammatic plan sketch of the device 1 according to the invention for thermal shock testing.

The present invention is suitable above all for testing the thermal stability of electronic components. It is also applicable, however, to any desired object, whose thermal stability is to be tested by the thermal shock method. The description which follows is intended, by way of example, to show a procedure and a design of the device according to the invention for testing electronic components. In FIG. 1, the device 1 and a corresponding procedure are shown diagrammatically. In this case, the heat exchanger zone comprises two separate chamber areas: the cold trap chamber and the drying chamber. (However, as already mentioned above, embodiments are also possible in which these two chambers are located directly side by side and thus occupy a single coherent chamber area, which is divided into two chambers only by a wall).

In the device 1 (FIG. 1), a drying chamber (A), a cold bath chamber (B), a cold trap chamber (C) and a hot bath chamber (D) are arranged in such a way that the drying chamber (A) and the cold trap chamber (C) on the one hand, and the cold bath chamber (B) and the hot bath chamber (D) on the other hand are located opposite each other. The cold bath chamber (B) is connected via closable openings (O) to the drying chamber (A) and to the cold trap chamber (C), and the hot bath chamber (D) is connected, likewise via closable openings (O), to the drying chamber (A) and to the cold trap chamber (C). Furthermore, the drying chamber (A) is accessible from the outside via a closable opening (O') in order to enable the basket (P) with the test specimens to be loaded and unloaded. The closable openings (O) and (O') are opened only briefly, if required, for the transport of the test specimens into the various chambers (A, B, C and D), so that, while the method proceeds, the individual chambers (A, B, C and D) are closed off from the outside and from one another.

In general, the closable openings (O) are iris diaphragms, which are each fitted to the ceiling of the individual chambers (A, B, C and D). The test specimens are in general transported on a holding device (H) in baskets and are introduced from above into the individual chambers (A, B, C and D) through the briefly opened iris diaphragms. In general, the holding device is composed of one or more arms which can be moved vertically and in a horizontal circle and on which the baskets are suspended. As a lifting/lowering and turning mechanism for the arms, a device known to those skilled in the art is used which comprises, for example, a hydraulic system and a motor. In this way, the baskets can be transported by the turning mechanism above the chambers A, B, C and D and introduced from above into the individual chambers and lifted out by means of the lifting/lowering mechanism.

Preferably, the baskets, which in general are closed at the top by a cover, are introduced into the particular bath from above through a tube (Z in FIG. 2) extending down into the bath liquid. In addition, the baskets generally have, at the upper rim, a sealing lip (L in FIG. 2) which seals the interspace between the basket and the tube.

The drying chamber (A) is in general heated by a plurality of opposite hot plates, in particular two, and with a fan, so that the basket with the test specimens in general is located for drying between the two hot plates. In the upper part of the drying chamber, a water cooler is in general fitted, on which the hot bath liquid, which initially adheres to the test specimens and to the basket and is then vaporized in the drying chamber, condenses and can then be returned via a pipe connection into the hot bath.

By means of this return of discharged hot bath liquid, a loss of bath liquid during the thermal shock test can be substantially avoided. The temperature of the drying chamber is in general 10° to 50° C., especially 10° to 20° C., higher than the temperature of the hot bath.

After the iris diaphragm has been opened, the basket with the test specimens is transported from the drying chamber (A) into the adjacent cold bath chamber (B) (FIG. 1). The iris diaphragms are closed again and the basket (P) with the test specimens is completely immersed in the cold bath liquid by means of the holding device. In general, the test specimens remain for at least five minutes in the cold bath liquid. The cold bath is in general cooled by the first vaporizer stage of a two-stage compression refrigeration unit. The cold trap, adjacent to the cold bath chamber, in the cold trap chamber (C) is cooled by the second vaporizer stage. This has the result that the temperature of the cold trap is 5 to 30 K (5° to 30° C.), especially 5 to 10 K (5° to 10° C.), lower than the temperature of the cold bath. After the test specimens have been cooled in the cold bath, they are withdrawn again, in the basket on the holding device, from the cold bath liquid and, after the iris diaphragms have been opened, transported from the cold bath chamber (B) into the cold trap chamber (C) (FIG. 1). The iris diaphragms are then closed again. In the cold trap chamber (C), the readily volatile compound which is in general used as the cold bath liquid and which still adheres to the test specimens and to the holding device including the basket, evaporates and condenses in the cold trap. The condensed cold bath liquid is collected at the bottom of the cold trap and pumped back, in general by means of a pump, via a pipe connection into the cold bath. Due to the return of discharged cold bath liquid, a loss of bath liquid during the thermal shock test is largely avoided.

After the iris diaphragms of cold trap chamber (C) and of hot bath chamber (D) have been opened, the basket with the test specimens is then transported into the hot bath chamber (D) (FIG. 1). The iris diaphragm is closed again and the basket with the test specimens is completely immersed in the hot bath liquid by means of the holding device.

In general, the test specimens remain for at least five minutes in the hot bath. The hot bath is in general heated by a hot plate. After the test specimens have been heated, these are withdrawn again, in the basket on the holding device, from the hot bath liquid and, after the iris diaphragm has been opened, transported from the hot bath chamber (D) into the drying chamber (A) (FIG. 1). After this, the iris diaphragms are closed again.

The change of the test specimens from the cold bath into the hot bath and vice versa—via the cold trap or the drying chamber respectively—should in general take at most about 10 seconds in each case, Moreover, in the method according to the invention, preferably two baskets with test specimens are used, which are fixed to opposite ends of the holding device and of which one is immersed into the cold bath and the other simultaneously in the hot bath. For the bath change of the test specimens, the iris diaphragms required for this purpose in each case are opened, and closed again after the change. The result of this is that the test specimens are essentially inside a closed space.

The arrangement and use, according to the invention, of the cold trap and drying chamber ensures that the two bath liquids essentially do not mix. The additional use of the preferred embodiments of the cold bath according to FIGS. 2 and 3, ensures that, especially in the case of a single test liquid for both baths, the temperature of the cold bath is also maintained for a longer operating period, because of the improved heat transfer.

Figure 2:
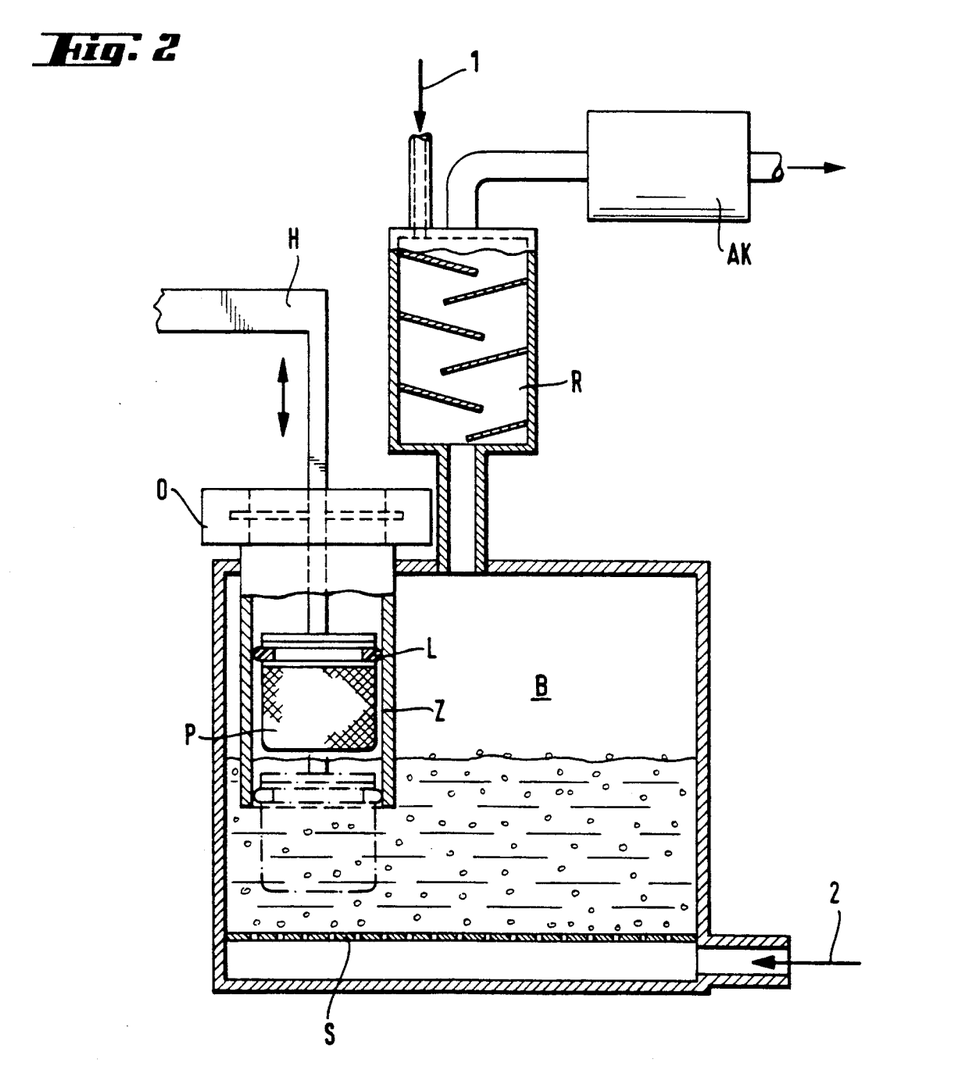
FIG. 2 is a diagrammatic side view of the cold bath with double bottom, downward-flow column and activated carbon filter.
Figure 3:
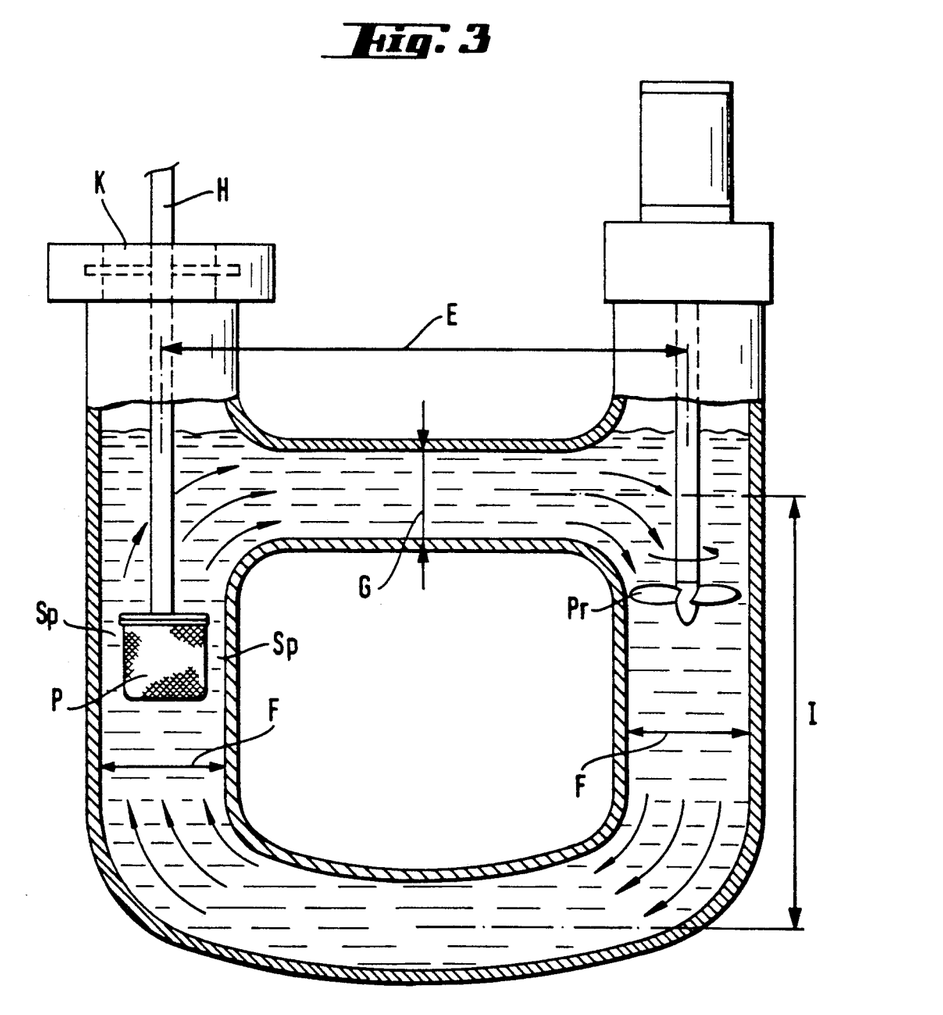
FIG. 3 is a diagrammatic side view of a bath vessel in the form of a pipe loop.

As an alternative thereto, the embodiments of the cold bath according to FIGS. 2 and 3 for the thermal shock test without using a cold trap and drying chamber, can be combined with only the hot bath.

The temperature of the cold bath is in general 0° to $-195°$ C., preferably $-40°$ to $-100°$ C., especially $-55°$ to $-65°$ C. The temperature of the hot bath is in general 0° to 500° C., preferably 0 to 300° C., especially 0° to 200° C. The temperature difference just mentioned must here be maintained.

In general, however, the cold bath liquids have a relatively high viscosity. Thus, the flowability of the bath liquid diminishes from a kinematic viscosity of about 150 mm$^2$/s to such an extent that, due to the low circulation rate of the bath liquid, the temperature in the cold bath gradually rises.

Because of their inert chemical behavior towards materials, because of their good thermal stability and because of their relatively high volatility, perfluorinated organic compounds have proved suitable as bath liquids. Preferably, the following perfluorinated organic compounds are employed:

1. Straight-chain or branched perfluoroalkanes of the formula $C_iF_{2i+2}$, i being an integer from 5 to 20. The preparation of the perfluoroalkanes has been described, for example, in German Offenlegungsschrift 2,332,097 and in EP-A-0,286,131.

In general, the perfluoroalkanes have a low boiling point and a low kinematic viscosity (less than 2 mm$^2$/s at 20° C.) and are therefore preferably suitable as cold bath liquids, for example perfluoropentane $C_5F_{12}$ having a boiling point of 30° C., perfluorohexane $C_6F_{14}$ having a boiling point of 56° C., perfluoro-2-methylpentane $C_6F_{14}$ having a boiling point of 58° C., perfluorooctane $C_8F_{18}$ having a boiling point of 102° C., perfluoro-2,3,4-trimethylpentane $C_8F_{18}$ having a boiling point of 115° C., perfluoro-2,4-dimethyl-3-ethylpentane $C_9F_{20}$ having a boiling point of 121° C.

2. Cyclic or substituted cyclic perfluoroalkanes having a carbon number from 10 to 20, for example perfluorodecalin, perfluorobutyldecalin, perfluoroperhydrophenanthrene and perfluoroperhydrobenzanthrene. Their preparation is described, for example, in German Offenlegungsschrift 2,000,830, U.S. Pat. No. 4,777,304, EP-A-0,253,529, EP-A-0,190,393 and in "Tetrahedron", 19, 1893 (1963).

The cyclic and substituted cyclic perfluoroalkanes have in general a high boiling point and a higher kinematic viscosity (greater than 8 mm$^2$/s at 20° C.) than the a cyclic perfluoroalkanes and are therefore especially suitable as hot bath liquids, for example perfluorotetradecahydrophenanthrene $C_{14}F_{24}$ having a boiling point of 215° C., perfluorobutyldecaline $C_{14}F_{26}$ which is an isomer mixture having a boiling range from 210° to 216° C., perfluoroperhydrobenzanthrene isomer mixture $C_{17}F_{28}$ having a boiling range from 259.5° to 263.5° C.

3. Perfluoropolyethers of the formula (I)

in which:

$R^1$ and $R^2$ which are identical or different are F or $C_aF_{2a+1}$, a being an integer from 1 to 10, and m and n are integers from 0 to 12 with $1 \leq n+m \leq 15$, or perfluoropolyethers of the formula (II)

$$R^3-O-(A)-(B)-(C)-R^4 \quad (II)$$

in which:

$R^3$ and $R^4$ which are identical or different are $C_bF_{2b+1}$, b being an integer from 1 to 4, (A), (B) and (C), which are different from one another, are a group of the formula $R^5$ being F or $CF_3$, d being an integer from 1 to 7 and e and f, which are identical or different, being integers from 0 to 7.

The preparation of perfluoropolyethers of the formulae (I) and (II) has been described, for example, in U.S. Pat. Nos. 3,665,041 and 3,985,810 and in Japanese Published Application Sho 58-103,334.

The perfluoropolyethers of the formulae (I) and (II) have in general a boiling point above about 130° C. and are therefore preferably suitable as hot bath liquids, especially if the boiling point is above about 170° C., for example the following compounds of the formula (I)

perfluoro-5,6,9-trimethyl-4,7,10-trioxatridecane having a boiling point of 175° C. (®Hostinert 175), perfluoro-5,8,9,12-tetramethyl-4,7,10,13-tetraoxahexadecane having a boiling point of 216° C. (®Hostinert 216), perfluoro-5,8,9,12,15-pentamethyl-4,7,10,13,16-pentaoxanonadecane having a boiling point of 245° C. (®Hostinert 245), perfluoro-5,8,11,12,15,18-hexamethyl-4,7,10,13,16,19-hexaoxadocosane having a boiling point of 272° C. (®Hostinert 272), perfluoro-5,8,11,14,15,18,21,24-octamethyl-4,7,10,13,16,19,22,25-octaoxaoctacosane having a boiling point of 316° C. (®Hostinert 316), or a mixture of perfluoropolyethers according to formula (II), in whose structural formulae $R^3$ and $R^4$ are $CF_3$, d is about 40, d:f is 5:1 to 20:1 and e is 0, having a boiling point of about 215° C.

In general, the kinematic viscosity of the perfluoropolyethers according to formula (I) or (II) is greater than 2 mm²/s at 20° C. and increases with rising boiling point of the compounds. In the use as hot bath liquids, this relatively high viscosity is, however, in general not of great importance, because the high bath temperature reduces again the viscosity of the liquid.

Particularly preferred hot bath liquids are perfluoropolyethers of the formula (I) of the ®Hostinert type, since the ®Hostinert types show a high thermal stability up to about 350° C.

Perfluoropolyethers of the formula (I) can, however, also be used as cold bath liquids, such as, for example, perfluoro-5,6-dimethyl-4,7-dioxadecane (®Hostinert 130).

4. Perfluorinated amines of the formula $$R^6R^7R^8N.$$

in which:

$R^6$ to $R^8$ which are identical or different are a group of the formula $C_gF_{2g+1}$, g being an integer from 1 to 14.

The preparation of the perfluorinated amines has been described, for example, in U.S. Pat. No. 2,616,927, German Offenlegungsschrift 3,804,473 and in EP-A-0,271,272.

The triperfluoroalkylamines of the formula $C_5F_{11}N(C_2F_5)_2$ (boiling point 215° C.) and $C_{10}F_{21}N(C_2F_5)_2$ (boiling point 238° C.) are preferably suitable as hot bath liquids at temperatures above about 200° C., since their kinematic viscosity is greater than 10 mm²/s (room temperature).

5. Perfluoroaminoethers of the formula in which:

$R^9$ to $R^{12}$ which are identical or different and are a group of the formula $C_gF_{2g+1}$, g being an integer from 1 to 14, and h and i which are identical or different and are an integer from 1 to 6.

The preparation of the perfluoroaminoethers has been described, for example, in EP-A 0,214,852. The perfluoroaminoethers are especially suitable as hot bath liquids, for example $(C_2F_5)_2NCF_2CF_2OCF_2CF_2N(C_3F_7)_2$ having a boiling point between 195° and 200° C., $(C_2F_5)_2NCF_2CF_2OCF_2CF_2N(C_4F_9)_2$ having a boiling range from 215° to 230° C.

$(C_3F_7)_2NCF_2CF_2OCF_2CF_2N(C_3F_7)_2$ having a boiling range from 225°-240° C., $(C_3F_7)_2N(CF_2)_4O(CF_2)_4N(C_3F_7)_2$ having a boiling range from 240° to 260° C. and $(C_3F_7)_2N(CF_2)_3O(CF_2)_3N(C_3F_7)_2$ having a boiling range from 240° to 265° C.

Not only the absolute temperature of the cold bath and hot bath, but also the relative temperature difference between cold bath and hot bath are decisive for the thermal shock test. In general, the thermal shock test provides more information, the greater is the temperature difference between the cold bath and the hot bath. By means of the thermal shock test according to the invention, using the abovementioned perfluorinated compounds as bath liquids, particularly large temperature differences of, for example, more than 200° C. can be reached and maintained without breakdowns in operation and without substantial mixing of the two bath liquids for the entire running time of the thermal shock test.

If two liquids are used, a liquid having the lowest possible viscosity will be selected for the cold bath, because of the better heat transfer. This is hardly possible if a single liquid is used for both baths, because the selection of the liquid is determined by its boiling point on account of the high temperature in the hot bath. In this case, the heat transfer must be improved by other measures described below. In fact, in the case of cold bath liquids having a kinematic viscosity greater than 150 mm$^2$/s below $-50°$ C., the cooling effect of the cold bath is in general poorer than in the case of less viscous bath liquids. For this reason, cold gaseous nitrogen is additionally introduced into the cold bath liquid in the special embodiment according to FIG. 2, in order to enhance the cooling effect. In general, the cold bath vessel has a double bottom, the upper bottom of which is preferably constructed as a perforated plate (S) (FIG. 2). The nitrogen gas (2) introduced between the bottoms flows in a finely disperse form through this perforated plate into the cold bath liquid. Preferably, the nitrogen gas stream is so strong that a turbulent flow is generated in the bath liquid, which leads to a substantially uniform temperature distribution within the cold bath and thus ensures a substantially constant cooling effect of the cooling bath during the thermal shock test. The installation of an additional agitator can in general be omitted in this embodiment.

In general, the nitrogen gas is enriched with bath liquid after it has left the cold bath. Preferably, this nitrogen gas stream is therefore passed through a downward-flow column (R), through which liquid nitrogen (1) flows in counter-current. The bath liquid is thus essentially scrubbed out of the nitrogen gas stream. Any vapors still present can be adsorbed on an activated carbon filter (AK), which is arranged downstream of the downward-flow column. The activated carbon filter can be regenerated, for example by steam, and the adsorbed bath liquid can then be recovered by generally known methods.

After it has passed through the downward-flow column, the liquid nitrogen is introduced into the cold bath liquid. By means of an appropriately selected feed rate of the liquid nitrogen, the bath liquid can be held at the required temperature for the entire operating period of the thermal shock test. As a result, additional cooling of the cold bath is in general unnecessary.

In the special embodiment according to FIG. 3, the heat transfer is improved in the following way:

To increase, the local circulation rate on the test specimens, they are introduced into a pipe loop as the cold bath chamber or hot bath chamber, in which loop the appropriate bath liquid is circulating (FIG. 3). The geometrical parameters of the pipe loop are, for example as in FIG. 3: E=630 mm, F=150 mm, G=100 mm and I=500 mm. In general, the test specimens are introduced in a circular-cylindrical basket through a closable opening (K) into the pipe loop. The bath liquid is in general circulated by means of an axial-flow pump or a propeller stirrer (Pr). A higher local circulation rate is achieved because of the reduction of the free cross-section of the pipe loop by the test specimens and the holding device. The cooling or heating of the bath liquid is carried out as explained above in the description. In order to further increase the local circulation rate, the gap (Sp) between the pipe loop and the basket can be closed. As a result, the bath liquid flows essentially through the basket directly past the test specimens at an increased velocity. This gives a particularly intensive heat transfer between the test specimens and the cold bath liquid or hot bath liquid. If a single liquid is used for both baths, it is sufficient to use one of the two special embodiments of the cold bath. Since no mixing of two different liquids is possible in this case, the installation of heat exchangers is unnecessary. As a result, the structure of such a thermal shock unit is simplified and the costs of manufacturing it are reduced.

EXAMPLES

Example 1

Figure 4:
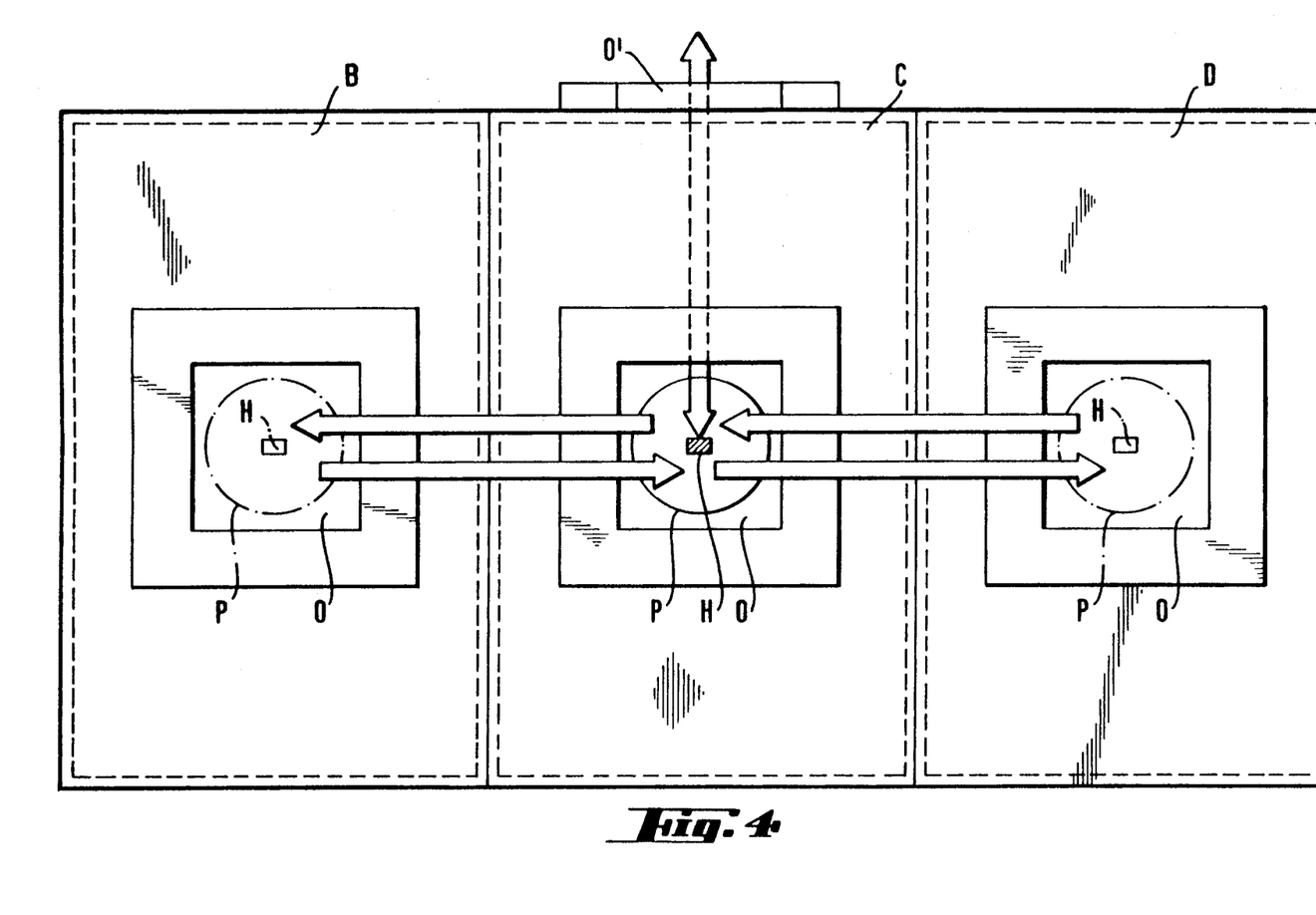
FIG. 4 is a diagrammatic plan sketch of the device 1 in a form with a cold trap, but without a drying chamber.

In an apparatus which is diagrammatically shown in FIG. 4 and which corresponds to device 1 in a design with a cold trap but without a drying chamber, the following test according to the description of device 1 was carried out. A perfluorinated compound, ®Hostinert 272 having a boiling point of 272° C., was used for the hot bath. The temperature of the hot bath was +250° C. A perfluorinated compound, ®Hostinert 130 having a boiling point of +130° C., was used for the cold bath. The temperature of the cold bath was −65° C. At this temperature, the cold bath liquid had a kinematic viscosity of 38 mm$^2$/s. The temperature of the cold trap was 75° C. The two baskets were loaded with electronic components, namely ceramic plates with gold-plated pins and chips cemented to the plates. 15 cycles were carried out per test. In one cycle, the baskets with the components remained for 5 minutes each in the hot bath and cold bath. The bath change of the baskets took about 10 seconds. The duration of a test including loading and unloading was 2 hours and 37 minutes. A total of 27 tests of 15 cycles each were carried out successively. The operating time was accordingly 70 hours and 44 minutes. Subsequently, the composition of the hot bath and cold bath and of the condensate in the collection space of the cold trap chamber (C) was analyzed by gas chromatography. The following compositions were found:

| in the hot bath | 97.0 area % of the hot bath liquid |
| | 3.0 area % of the cold bath liquid |
| in the cold bath | 100.0 area % of the cold bath liquid. | in the condensate of the collection space of the cold trap
96.7 area % of the cold bath liquid
3.2 are % of the hot bath liquid.

Thus the cold bath liquid remained unchanged during the operation lasting more than 70 hours, while a small quantity of cold bath liquid was entrained into the hot bath. If the test had been continued, however, this small quantity would have been largely condensed out in the cold trap. It may therefore be assumed that the liquid phase of the hot bath during prolonged operation would also contain no cold bath liquid, because the boiling point of the latter should be far below the temperature in the hot bath. In this example, the temperature difference was 120 K (120 Celsius degrees). For a quantitative determination of the hot bath vapors, these were, in this test, not returned as condensate into the hot bath, but largely condensed in the cold trap. Owing to the closed system, no substantial losses of the two bath liquids occurred overall during the test.

Example 2

This test series, carried out in a cold bath according to FIG. 2, investigates the effect of gaseous and liquid nitrogen on the cold bath liquid. The cold bath liquid used was the perfluorinated compound ®Hostinert 130 having a boiling point of 130° C. In this test series, however, no basket with test specimens was immersed in the cold bath liquid. In the first part of the test series, a total of 200 l of nitrogen gas was blown in the course of one hour through the perforated plate (S) from below into the cold bath liquid (250 ml) at room temperature (27° C.). Subsequently, the activated carbon filter (AK) was weighed. Its increase in weight was 23.7 % by mass.

This test shows that a relatively large quantity of the cold bath liquid is carried over at room temperature by the nitrogen gas stream and retained on the activated carbon filter.

In the second part of this test series, 200 l of nitrogen gas was blown, as in the first part of the test series, in the course of one hour from below into the same cold bath liquid, but additionally 280 ml of liquid nitrogen were also introduced in counter-current to the emerging nitrogen gas from above through a heat-insulated downward-flow column (R) and then in heat-insulated lines into the cold bath liquid. During the entire operating period, the cold bath liquid was at a temperature of −65° C. At the end of the test, the change in weight of the activated carbon filter (AK) was determined. The increase in weight was 0.98 % by mass.

This test shows that, by feeding 280 ml/h of liquid nitrogen, a cold bath temperature of −65° C. was reached and maintained throughout the entire duration of the test. Additional indirect cooling was not necessary. The test also shows that as a result of the use of a downward-flow column in combination with liquid nitrogen only a small quantity of cold bath liquid passes into the activated carbon filter.

Example 3

The test was carried out in an apparatus, diagrammatically shown in FIG. 4, with a cold bath as shown in FIG. 2, and analogously to the test conditions of Example 1. In this case, 200 l/h of nitrogen gas (2) were additionally introduced from below through the perforated plate (S), and 280 ml/h of liquid nitrogen were introduced from above in counter-current via the downward-flow column (R) into the cold bath liquid (250 ml). Throughout the entire duration of the test, a constant temperature of +250° C. in the hot bath and of −65° C. in the cold bath was always maintained. At the end of the test, the increase in weight of the activated carbon filter (AK) and the composition of the hot bath and cold bath and of the condensate in the collection space of the cold trap (C) were analyzed by gas chromatography.

The following compositions were found:

| in the hot bath | 97.0 area % of the hot bath liquid |
| | 3.0 area % of the cold bath liquid |
| in the cold bath | 100.0 area % of the cold bath liquid. | in the condensate of the collection space of the cold trap
99.9 area % of the cold bath liquid
0.1 area % of the hot bath liquid
increase in weight of the activated carbon filter
78.8 % by mass (average/h: 1.1 % by mass)

Example 4

The test was carried out in an apparatus shown in FIG. 3, and the effect of a restriction of the cross-section of the pipe loop by a circular-cylindrical mesh unit was investigated as a function of the circulation capacity of the propeller stirrer and of the viscosity of the bath liquid. An apparatus according to FIG. 3, having the equipment parameters indicated in the description, was used for the test. The circular-cylindrical mesh unit of PMMA (P), which in this test replaced the basket with the test specimens, had a diameter of 85 mm, a height of 80 mm and a square passage width of 6×6 mm$^2$. The web width of the mesh was 3 mm. After the mesh unit had been introduced into the pipe arm having the closable opening (K) the annular gap (Sp) remaining between the pipe and the mesh unit was closed by a steel ring. The total circulating stream of the bath liquid was therefore able to flow only through the mesh unit (P). The rate of the circulating stream was regulated by means of a 3-blade propeller stirrer having a blade inclination of 25° in the manner of a marine screw, driven by an electric motor. The liquid throughput V as a function of the specific power $P_V$ of the propeller stirrer was measured for two bath liquids of different viscosity. In the first test series, water was used as the bath liquid ($\eta=1$ mPa.s; 20° C.), and a 72% glycerol/water solution ($\eta=26$ mPa.s; 20° C.) was used in the second test series. The dynamic liquid viscosity was measured by the falling-ball method using a Höppler viscometer. In both test series, the liquid throughput V was measured both in the presence and in the absence of the mesh unit and of the steel ring.

1. Test series with water as bath liquid (1 mPa·s)

| | $P_V$ [kW/m$^3$] | V [m$^3$/h] |
|---|---|---|
| 1. Test series with water as bath liquid (1 mPa · s) | | |
| without mesh unit | 0.1 | 13.2 |
| " | 1.0 | 29.1 |
| with mesh unit | 0.1 | 9.1 |
| " | 1.0 | 17.0 |
| 2. Test series with 72% glycerol solution (26 mPa · s) | | |
| without mesh unit | 0.1 | 7.2 |
| " | 1.0 | 21.0 |
| with mesh unit | 0.1 | 3.4 |
| " | 1.0 | 10.5 |

As expected, the throughput of bath liquid V is higher without mesh unit and at low viscosity than with mesh unit and at high viscosity.

As a result of the reduction in the cross-section of the pipe loop at the site where the mesh unit with the cover ring is positioned, the velocity of the bath liquid increases locally. Thus, the local velocity of 0.20 m/s (without mesh unit) rose to 1.25 m/s (with mesh unit and cover ring) at a throughput of 14 m$^3$/h At a throughput of 15 m$^3$/h, the residence time of the bath liquid in the mesh unit was 0.1 second.

We claim:
1. A method for testing objects by subjecting them to thermal shock in a normally closed apparatus, said normally closed apparatus comprising:
   (1) a hot bath chamber provided with a normally closed opening therein for admitting the object to be tested and for closing to isolate said object from the rest of the apparatus, said hot bath chamber containing a hot bath liquid and being provided with a device for heating the hot bath liquid, (2) a drying chamber provided with a normally closed opening therein for admitting the object to be tested and for closing to isolate said object from the rest of the apparatus, the temperature of said drying chamber being 10° to 50° C. higher than the temperature of the hot bath liquid, (3) a cold bath chamber provided with a normally closed opening therein for admitting the object to be tested and for closing to isolate said object from the test of the apparatus, said cold bath chamber containing a cold bath liquid, the temperature difference between the hot bath liquid and cold bath liquid being 50° to 500° C., said cold bath chamber being provided with a device for cooling the cold bath liquid, (4) a cold trap chamber provided with a normally closed opening therein for admitting the object to be tested and for closing to isolate said object from the rest of the apparatus, the temperature in the cold trap chamber being 5° to 30° C. lower than the temperature of the cold bath liquid; said method comprising:

subsequent to the introduction of the object to be tested into the normally closed apparatus, initiating at least one cycle comprising a sequence comprising cooling, first drying, heating, and second drying steps or a sequence comprising heating, first drying, cooling, and second drying steps, by:

(i) introducing the object to be tested into the cold bath chamber and cooling the object by immersion in the cold bath liquid, then (ii) introducing said object into the cold trap chamber and drying said object therein, then (iii) introducing said object into the hot bath chamber and heating said object by immersion in the hot bath liquid, then (iv) introducing said object into the drying chamber and drying said object therein, the first such cycle beginning with introduction into the cold bath chamber or with introduction into the hot bath chamber.

2. The method as claimed in claim 1 wherein the cycle comprising said sequence which is initiated subsequent to introduction of said object into said apparatus comprises:

(i) cooling said object by immersion in the cold bath liquid, (ii) drying said object in the cold trap chamber, (iii) heating said object by immersion in the hot bath liquid, and (iv) drying said object in the drying chamber, and wherein said cycle is carried out repeatedly.

3. The method as claimed in claim 1 wherein the cycle comprising said sequence which is initiated subsequent to introduction of said object into said apparatus comprises:

(i) heating said object by immersion in the hot bath liquid, (ii) drying said object in the drying chamber,

(iii) cooling the object by immersion in the cold bath liquid, and (iv) drying said object in the cold trap chamber, and wherein said cycle is carried out repeatedly.

4. The method as claimed in claim 1, wherein gaseous and/or liquid nitrogen is introduced into the cold bath liquid.

5. The method as claimed in claim 1 wherein at least one of the two bath chambers is a pipe loop with said normally closed opening fitted at an upper portion of the pipe loop such that said object can be admitted through said normally closed opening into the pipe loop, and wherein a stirrer device is fitted in the pipe loop.

6. The method as claimed in claim 1, wherein the cold bath liquid comprises a straight-chain or branched perfluoroalkane of the formula $C_iF_{2i+2}$, i being an integer from 5 to 20, or a perfluoropolyether of the formula (I)

in which:
$R^1$ and $R^2$ which are identical or different are F or $C_aF_{2a+1}$, a being an integer from 1 t 10, and m and n are integers from 0 to 12 with $1 \leq n+m \leq 15$, or a perfluoropolyether of the formula (II)

in which:
$R^3$ ad $R^4$ which are identical or different are $C_bF_{2b-1}$, b being an integer from 1 to 4,
(A), (B) and (C), which are different from one another, are a group of the formula $R^5$ being F or $CF_3$,
d being an integer from 1 to 7 and
e and f, which are identical or different, being an integer from 0 to 7.

7. The method as claimed in claim 1, wherein the hot bath liquid comprises a cyclic or substituted cyclic perfluoroalkane having a carbon number from 10 to 20 or perfluoropolyethers of the formula (I)

in which:
$R^1$ and $R^2$ which are identical or different are F or $C_aF_{2a+1}$, a being an integer from 1 to 10, and m and n are integers from 0 to 12 with $1 \leq n+m \leq 15$, or a perfluoropolyether of the formula (II)

in which:
$R^3$ and $R^4$ which are identical or different are $C_bF_{2b+1}$,
b being an integer from 1 to 4,
(A), (B) and (C), which are different from one another, are a group of the formula $R^5$ being F or $CF_3$, d being an integer from 1 to 7 and e and f, which are identical or different, being an integer from 0 to 7, or a perfluorinated amines of the formula $$R^6R^7R^8N.$$

in which:

$R^6$ to $R^8$ which are identical or different are a group of the formula $C_gF_{2g+1}$, g being an integer from 1 to 14, or a perfluoroaminoether of the formula in which:

$R^9$ and $R^{12}$ which are identical or different are a group of the formula $C_gF_{2g+1}$, g being an integer from 1 to 14, and h and i which are identical or different are an integer from 1 to 6.

8. The method as claimed in claim 1, wherein both the cold bath liquid and the hot bath liquid comprise a perfluoropolyether of the formula (I)

in which:

$R^1$ $R^2$ which are identical or different are F or $C_aF_{2a+1}$, a being an integer from 1 to 10, and m and n are integers from 0 to 12 with $1 \leq n+m \leq 15$, or a perfluoropolyether of the formula (II)

$$-R^3-O-(A)-(B)-(C)-R^4 \qquad (II)$$

in which:

$R^3$ and $R^4$ which are identical or different are $C_bF_{2b+1}$, b being an integer from 1 to 4, (A), (B) and (C), which are different from one another, are a group of the formula $R^5$ being F or $CF_3$, d being an integer from 1 to 7 and e and f, which are identical or different, being an integer from 0 to 7.

9. A device for testing objects by subjecting them to thermal shock in a normally closed apparatus, said closed apparatus comprising:

an outer wall surrounding at least four chambers disposed within said apparatus, said chambers comprising:

(1) a hot bath chamber provided with a normally closed opening therein for admitting the object to be tested and for closing to isolate said object from the rest of the apparatus, said hot bath chamber being provided with a device for heating the hot bath liquid, (2) a drying chamber provided with a normally closed opening therein for admitting the object to be tested and for closing to isolate said object from the rest of the apparatus, (3) a cold bath chamber provided with a normally closed opening therein for admitting the object to be tested and for closing to isolate said object from the rest of the apparatus, said cold bath chamber being provided with a device for cooling the cold bath liquid, (4) a cold trap chamber provided with a normally closed opening therein for admitting the object to be tested and for closing to isolate said object from the rest of the apparatus;

a transporting device for transporting the objects to be tested from chamber to chamber, beginning with the cold bath chamber or the hot bath chamber, and proceeding in the sequence cold bath chamber, cold trap chamber, hot bath chamber, drying chamber, or in the sequence hot bath chamber, drying chamber, cold bath chamber, cold trap chamber;

said outer wall having a normally closed opening therein for loading the transporting device with at least one object to be tested and for unloading said object from the transporting device after said testing is completed.

10. The device as claimed in claim 9, wherein the apparatus further comprises a staged compression refrigeration unit having a first vaporizer stage and a second vaporizer stage for cooling the cold bath chamber and the cold trap chamber, the cold bath chamber being cooled by the first vaporizer stage and the cold trap chamber being cooled by the second vaporizer stage.

11. The device as claimed in claim 9, wherein the cold bath chamber has the normally closed opening in the ceiling thereof; wherein the floor of said chamber comprises a double bottom comprising an upper bottom and a lower bottom, the upper bottom being a perforated plate, and wherein cooling gas supply line communicates with the space defined by the upper bottom and the lower bottom.

12. The device as claimed in claim 9, wherein at least one of the two bath chambers is a pipe loop with the normally closed opening fitted in an upper portion thereof, said pipe loop further comprising a stirrer disposed therein.

* * * * *